United States Patent
Deister et al.

(10) Patent No.: US 9,629,997 B2
(45) Date of Patent: Apr. 25, 2017

(54) MATERIALS AND METHODS FOR PROTECTING AGAINST NEUROMAS

(71) Applicant: AXOGEN, INC., Alachua, FL (US)

(72) Inventors: Curt Deister, Alachua, FL (US); Crystal Simon, Alachua, FL (US)

(73) Assignee: AXOGEN CORPORATION, Alachua, FL (US)

(*) Notice: Subject to any disclaimer, the term of this patent is extended or adjusted under 35 U.S.C. 154(b) by 83 days.

(21) Appl. No.: 14/036,405

(22) Filed: Sep. 25, 2013

(65) Prior Publication Data
US 2014/0094932 A1 Apr. 3, 2014

Related U.S. Application Data
(60) Provisional application No. 61/705,251, filed on Sep. 25, 2012.

(51) Int. Cl.
*A61N 1/05* (2006.01)
*A61L 31/04* (2006.01)
(52) U.S. Cl.
CPC ............ *A61N 1/0558* (2013.01); *A61L 31/04* (2013.01); *A61N 1/05* (2013.01)
(58) Field of Classification Search
CPC A61F 2/04; A61N 1/05; A61N 1/0558; A61L 31/04
See application file for complete search history.

(56) References Cited

U.S. PATENT DOCUMENTS

| 4,778,467 A | 10/1988 | Stensaas et al. |
| 5,705,178 A | 1/1998 | Roufa et al. |
| 2006/0224242 A1* | 10/2006 | Swords et al. ............ 623/17.19 |
| 2010/0055149 A1* | 3/2010 | Li et al. .................... 424/425 |

FOREIGN PATENT DOCUMENTS

WO WO 2012/097297 A2 7/2012

OTHER PUBLICATIONS

Lewin-Kowalik et al. Prevention and Management of Painful Neuroma. Neuro Med Chir. 2006 (46):62-68.*
Ducic, Ivica et al. "The Role of Peripheral Nerve Surgery in the Treatment of Chronic Pain Associated with Stumps," *Plastic Reconstructive Surgery*, 2008, vol. 121, No. 3, p. 908-914.
(Continued)

*Primary Examiner* — Christopher D Prone
*Assistant Examiner* — Rokhaya Diop
(74) *Attorney, Agent, or Firm* — Saliwanchik, Lloyd & Eisenschenk

(57) ABSTRACT

The subject invention provides devices and methods for alleviating discomfort associated with neuroma formation. The devices and methods of the invention effectively use the body's natural response of reconstructing implanted biomaterials to minimize the size of, isolate, and protect a neuroma. In preferred embodiments, the subject device is a cylindrical cap, wherein the internal chamber of the cylindrical cap physically partitions the nerve to enable an arrangement of nerve fibers (as opposed to haphazardly arranged nerve fibers often produced in neuromas). In addition, the cap's material remodels into a tissue cushion after implantation, which protects the neuroma from being stimulated and inducing pain.

5 Claims, 3 Drawing Sheets

(56) References Cited

OTHER PUBLICATIONS

Lewin-Kowalik, Joanna et al. "Prevention and Management of Painful Neuroma," *Neurologia medico-chirurgica*, Feb. 2006, vol. 46, No. 2, p. 62-68.
Rajput, Kanishka et al. "Painful Neuromas: A Review," *Clinical Journal of Pain*, Sep. 2012, vol. 28, No. 7, p. 639-645.
Stokvis, Annemieke et al. "Surgical management of neuroma pain: A prospective follow-up study," *Pain*, Dec. 2010, vol. 151, No. 3, p. 862-869.

* cited by examiner

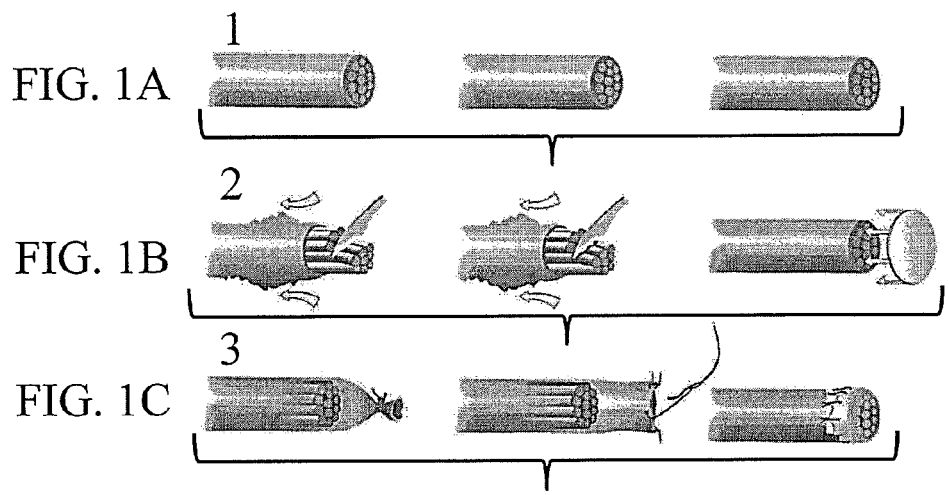
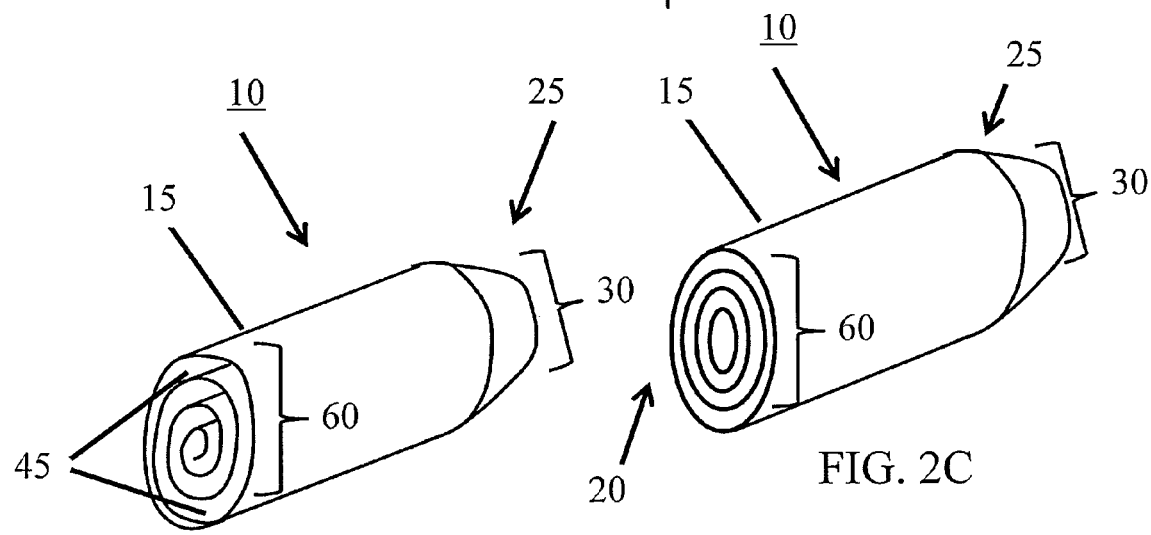

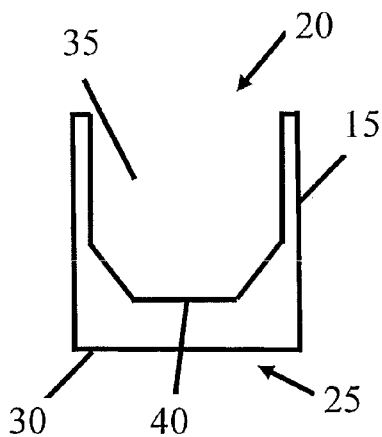
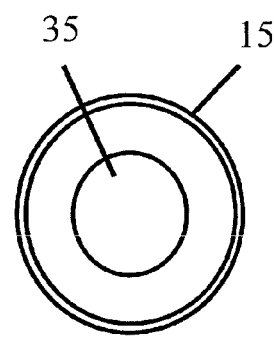
FIG. 3A
FIG. 3B
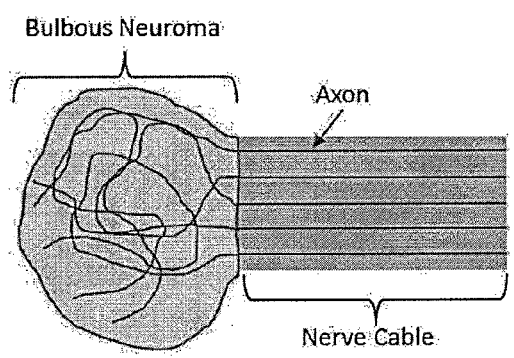
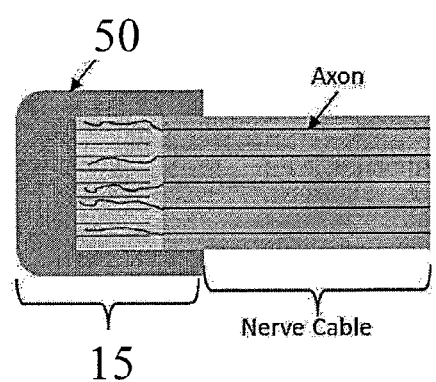
FIG. 4A
FIG. 4B

MATERIALS AND METHODS FOR PROTECTING AGAINST NEUROMAS

CROSS-REFERENCE TO A RELATED APPLICATION

This application claims the benefit of U.S. provisional application Ser. No. 61/705,251, filed Sep. 25, 2012, which is incorporated herein by reference in its entirety.

BACKGROUND OF INVENTION

Neuromas develop as a part of a normal reparative process following peripheral nerve injury. They are formed when nerve recovery towards the distal nerve end or target organ fails and nerve fibers improperly and irregularly regenerate into the surrounding scar tissue. Neuromas consist of a deranged architecture of tangled axons, Schwann cells, endoneurial cells, and perineurial cells in a dense collagenous matrix with surrounding fibroblasts (Mackinnon S E et al. 1985. Alteration of neuroma formation by manipulation of its microenvironment. *Plast Reconstr Surg.* 76:345-53). The up-regulation of certain channels and receptors during neuroma development can also cause abnormal sensitivity and spontaneous activity of injured axons (Curtin C and Carroll I. 2009. Cutaneous neuroma physiology and its relationship to chronic pain. *J. Hand Surg Am.* 34:1334-6). Haphazardly arranged nerve fibers are known to produce abnormal activity that stimulates central neurons (Wall P D and Gutnick M. 1974. Ongoing activity in peripheral nerves; physiology and pharmacology of impulses originating from neuroma. *Exp Neurol.* 43:580-593). This ongoing activity can be enhanced by mechanical stimulation, for example, from the constantly rebuilt scar at the injury site (Nordin M et al. 1984. Ectopic sensory discharges and paresthesiae in patients with disorders of peripheral nerves, dorsal roots and dorsal columns. *Pain.* 20:231-245; Scadding J W. 1981. Development of ongoing activity, mechanosensitivity, and adrenaline sensitivity in severed peripheral nerve axons. *Exp Neurol.* 73:345-364).

Neuromas of the nerve stump are unavoidable consequences of nerve injury when the nerve is not, or cannot be, repaired and can result in debilitating pain. This is particularly likely if the neuroma is present at or near the surface as physical stimulation induces signaling in the nerve resulting in a sensation of pain.

Neuroma prevention and attenuation strategies have used various methods to limit the size of the neuroma and protect the neuroma from external stimuli. Current prevention methods, see FIG. 1, attempt to limit the size of the neuroma and so reduce or limit possible communications between axons within the injured nerve site by limiting the number of other axons and axons contacts in the disorganized structure that characterizes neuromas. Due to a variety of factors, current methods of neuroma mitigation/prevention have an unacceptable level of efficacy.

While various methods to prevent, minimize, or shield neuromas have been attempted, the current clinical "gold standard" for treating neuromas is to bury the nerve end (that will form the neuroma) into muscle or a hole drilled in bone. The surrounding tissue cushions and isolates the neuroma so that it is not stimulated (so it does not cause painful sensations). However this procedure can greatly complicate the surgery as significant additional dissection of otherwise healthy tissue is required to place the nerve stump. For these reasons, placement of the nerve stump is often not performed in amputations (and many other nerve procedures) despite the fact that ~30% of neuromas become painful and problematic.

Another method used is to dissect the nerve stump back to leave a segment of epineurium overhanging and then ligate the overhanging epineurium, or covering the face of the nerve stump with the freed epineurium (or use a segment of the epineurium from the distal nerve). Yet another method that is commonly used today is a suture ligation. Basically, a loop of suture is placed around the end of the nerve and tightened. This pressure is then believed to mechanically block the exit of axons and eventually form scar tissue at the site. However clinical and pre-clinical evidence has shown that a painful neuroma can form behind a ligation. The ligated nerve is generally not positioned to minimize mechanical stimulation of the neuroma, though studies have shown that positioning the nerve in a protected area can resolve chronic stump pain.

Covering the nerve stump with a silicone rubber tube, a vein, or a silicone rubber plug (i.e. a tube with a sealed end) has also been used.

Current methods for addressing neuromas have not been generally successful and therefore not generally adopted.

BRIEF SUMMARY

The subject invention provides devices and methods for alleviating discomfort associated with neuroma formation. Specifically, the subject invention provides biomedical devices and methods for neuroma size limitation and neuroma protection.

In preferred embodiments, the subject device is a cylindrical cap to be applied to nerves within a subject's body (e.g., sterile), wherein the internal chamber of the cylindrical cap physically partitions the nerve to enable an arrangement of nerve fibers (as opposed to haphazardly arranged nerve fibers often produced in neuromas). Preferably the device is sterile. In addition, the cap's material remodels into a tissue cushion after implantation, which protects the neuroma from being stimulated and inducing pain. Preferably, the dimensions of the body of the device are: about 1 mm to 25 mm in diameter and 1 mm to 100 mm in length.

In a specific embodiment, the internal partitioning of the cap is in the form of a spiral channel. The material of the cap is a biomaterial that can remodel to generate a volume of protective connective tissue around a neuroma (rather than the current use of a biomaterial to contain a neuroma volumetrically). In a preferred embodiment, the material of the cap is a membrane biomaterial such as small intestine submucosa (SIS), amnion, dermis, or decellularized fascia.

In one embodiment of a method of use, a device is provided that contains a hollow indentation at one end to allow insertion of the nerve stump and a dense layer of biomaterial on the exterior surface to mechanically isolate the neuroma and prevent axons from escaping the device. The hollow indentation contains partitions to subdivide the neuroma that will form from the nerve stump. The nerve stump is secured in the hollow indentation. After the device is implanted, it is remodeled into the body's own tissue to provide a cushion for the neuroma.

The combination of limiting the growth of the neuroma through physical partitioning along with the creation of a connective tissue capsule is unique. This novel combination of features and design effectively uses the body's natural response of reconstructing implanted biomaterials to minimize the size of, isolate, and protect the neuroma.

BRIEF DESCRIPTION OF THE DRAWINGS

FIGS. 1A, 1B and 1C show schematic presentation of consecutive steps of various current nerve stump capping methods: Step 1—nerve transection; Step 2—nerve stump preparation (A and B, nerve sheath must be slid off, then a piece of the nerve is removed to prepare a sleeve-like fragment of epineurium; C, cap can be formed of any autologous tissue, sutured to the epineurium); Step 3—the end of epineurium can be tied up or sutured. Lewin-Kowalik J. et al. (2006) Prevention and Management of Painful Neuroma. *Neurol Med Chir* (Tokyo), 46:62-68.

FIGS. 2A, 2B and 2C show perspective views (2A and 2C) of two embodiments of the invention and a side view (2B) of an embodiment of the device of the subject invention.

FIGS. 3A and 3B show a side cut-away view (FIG. 3A) of and top view of the proximal end (FIG. 3B) of the embodiment.

FIG. 4A is a schematic drawing showing an untreated neuroma.

FIG. 4B is a schematic drawing showing a neuroma treated using an embodiment of a device of the subject invention.

DETAILED DISCLOSURE

Figure 5A:
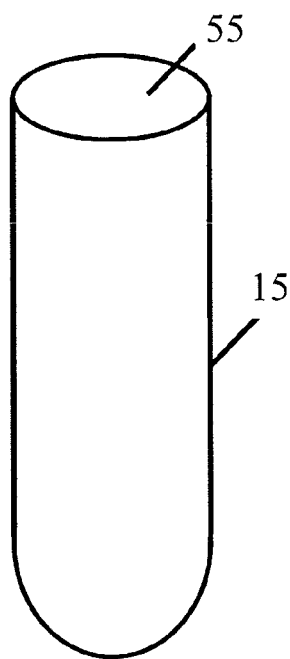
FIG. 5A is a schematic drawing showing a perspective view of another embodiment of the device of the invention.

The subject invention provides devices and methods for alleviating discomfort associated with neuromas. More specifically, the subject invention pertains to devices and methods for limiting neuroma size and physically surrounding the neuroma to prevent stimulation that elicits neuropathic pain. In certain embodiments, the subject invention is directed to a tissue-engineered scaffold that provides: a barrier limiting the size of a neuroma, subdivision of neuroma volume to reduce axonal cross-talk, and mechanical isolation of the neuroma.

A device of the subject invention is designed to become a protective, connective tissue capsule surrounding the neuroma. Within the volume created by the barrier, sub-dividing the injured nerve limits the amount of interaction between axons thereby limiting signaling cascades inside the neuroma that can be interpreted as pain when sensory neurons signaling occurs. By providing mechanical isolation, the subject device limits stimulation of the neuroma, which is a prominent cause of signaling cascades, which in turn are the direct cause of pain. The ability of the material of the subject device to bio-remodel into a native tissue cushion is another advantageous feature when combined with the physical partitioning of the axon stump.

This subject invention provides the benefits of epineural flap (or ligation) to limit neuroma size and bury the nerve in a mechanically isolated location in a single off-the-shelf device. This device isolates and protects the neuroma thereby preventing painful sensations without the need for any repositioning of the nerve. Instead, the device is secured to the stump of the nerve and then integrated into the host tissues.

A schematic of an embodiment of the subject invention is shown in FIGS. 2-4. In one embodiment illustrated in FIG. 2, the device 10 of the subject invention has a body 15 that comprises a proximal end 20 and a distal end 25.

It can be seen in FIG. 2 that one embodiment of the body 15 of the device 10 is cylindrical in shape. However, the shape of the body 15 of the device 10 can vary depending upon the type, diameter and location of a nerve stump, as well as other factors known to those with skill in the art. For example, the circumferential shape of the body can be variable and be, by way of non-limiting examples, an ovoid, circular, square, rectangular, triangular, or any other polygonal shape. In an exemplified embodiment, the circumferential shape of the body is generally circular.

The dimensions of the body can vary depending on the type, diameter and location of a nerve stump, as well as other factors known to those skilled in the art. The body of the device can have dimensions of approximately 1 mm to 25 mm in diameter and 1 mm to 100 mm length. The body of the device will typically be less than 100 mm in diameter and less than 500 mm in length.

In one embodiment, the diameter of the distal end 25 of the body 15 can be narrower than the diameter of the proximal end 20, as seen, for example, in FIGS. 2 and 3. In one embodiment, for example, as shown in FIG. 3, the proximal end 20 is open and the distal end 25 of the body 15 is closed off entirely 30 to form a cap. FIG. 3 also illustrates an embodiment in which a hollow indentation 35 is provided in the body 15. In certain embodiments, the interior surface of the closed off 30 portion of body 15 can be in the form of a bevel 40; alternatively, a closed off portion can be a flat surface.

According to one embodiment of the invention, the body 15 can include spiral partitions 45. Advantageously, the spiral partitions enable subdivision and arrangement of axons from the nerve stump. In certain related embodiments, the body comprises a tightly packed spiral of a solid sheet of biomaterial. Preferably, where the body comprises a tightly packed spiral of a solid sheet of biomaterial, there are no voids present that could lead to axonal escape from the device.

In one embodiment, as illustrated in FIG. 4B, an unchambered layer of biomaterial 50 is provided on the exterior surface of the chambered body 15 of the device. The biomaterial preferably isolates the neuroma and prevents axons from escaping the body 15 of the device. FIG. 4A is a schematic drawing showing an untreated neuroma.

Both natural and synthetic biomaterials can be used to manufacture the device of the subject invention. In certain embodiments, the biomaterial is a homogenous material. Examples of biomaterials for use in manufacturing the subject invention include, but are not limited to, high density polyethylene (HDPE), polyethylene glycol (PEG) hydrogel, purified proteins from human or animal sources (e.g., membrane of purified collagen or fibrin), and decellularized tissue constructs (e.g., demineralized bone, amnion, SIS, dermis, or fascia). An HDPE or PEG device can comprise or consist of a cylinder of porous HDPE or PEG surrounded by a layer of non-porous HDPE or PEG. Biomaterials which can form a fluid material, such as soluble purified collagen or particulate SIS and dermis, can be directly cast to form the device without a membrane as an intermediate.

In certain embodiments, the body of the device can be made by rolling a sheet of biomaterial to form spiral partitions. Where the body of the device is a "roll" of spiral partitions, the layers of the roll separate slightly to allow nerve regeneration to proceed a short distance into the device before encountering, and being stopped by, infiltrating non-nerve tissue (i.e. the rolled version has longitudinal pores or characteristics). In specific related embodiments, layers of the rolled biomaterial are situated such that a spiral channel is present on the face of the device facing the nerve stump but the device face external to the nerve sump is solid.

In other embodiments, the body of the device can be made of a porous biomaterial. In yet other embodiments, the body includes a hollow central cavity to facilitate insertion of a nerve stump. In certain other embodiments, a body is provided with a hollow cavity wherein layers of biomaterial scaffolding fill a portion of the hollow cavity to create a laminar or multi-laminar construct 60 (see FIG. 2C).

In an alternate embodiment as illustrated in FIG. 5A, the body 15 of the device resembles a test tube, where the body is made of a thin layer of biomaterial (either a single layer or a small number of layers) and there is a hollow central cavity 55 to facilitate insertion of a nerve stump.

Figure 5B:
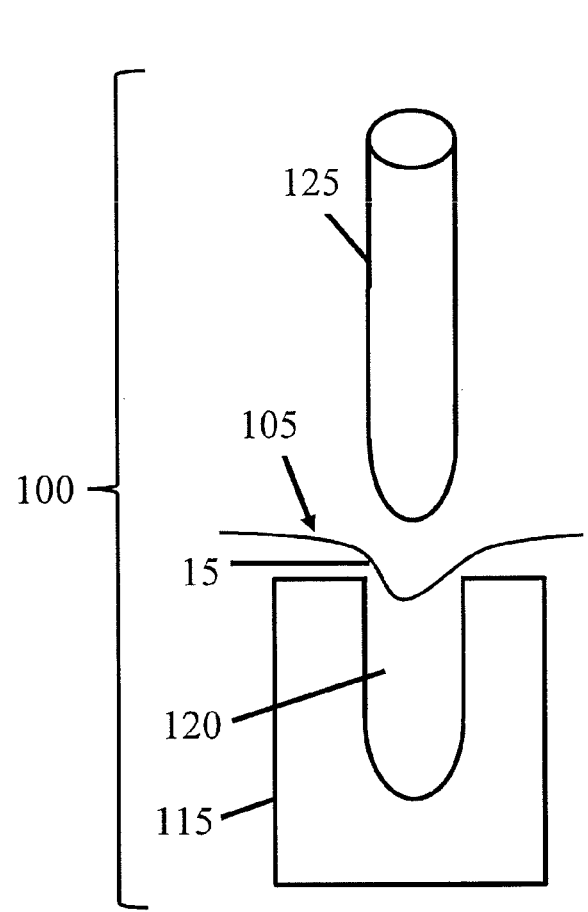
FIG. 5B is a view illustrating a press-forming process executed by the press-forming apparatus to manufacture an embodiment of the device shown in FIG. 5A.

Illustrated in FIG. 5B is a method for producing the embodiment of the device of FIG. 5A. FIG. 5B illustrates a press formation apparatus 100 for manufacturing the device of FIG. 5A. As shown in FIG. 5A, a thin layer of biomaterial 105 (either a single layer or a small number of layers of biomaterial) is mounted on a receiving portion 115 of the press formation apparatus 100. The receiving portion 115 has an opening 120 for receiving a punch 125, where the shape of the opening 120 corresponds with that of the punch 125. The receiving portion 115 and the punch 125 can be manufactured by die molding. Preferably, the punch 125 is rod shaped; however, other shapes known to the skilled artisan can be used for the opening of the receiving portion and the punch.

The thin layer of biomaterial 105 is arranged over the opening 120 of the receiving portion 115. Once the biomaterial 105 is positioned, the punch 125 is then driven downward and received in the opening 120. In this way, the body 15 of the device is formed.

In further embodiments, a cylindrical body having a hollow interior with open ends is provided. The distal end of the body may be "crimped" during the manufacturing process to present a more solid biomaterial as a barrier to axonal escape from the device. An example is the use of a crimped mold during vacuum pressing of a rolled cylinder, such that one end is of a smaller diameter.

In a preferred embodiment, the body of the subject device comprises a cylinder of SIS. A hollow cavity is provided at the proximal end to allow insertion of a nerve stump. A deep spiral partition is present in the body to subdivide the neuroma that will form from the nerve stump, and a dense layer of biomaterial is provided on the entire exterior surface to mechanically isolate the neuroma and prevents axons from escaping the device.

In a method of use, a nerve stump is secured in the hollow indentation by means of a suture, staple, clip, or surgical adhesive or sealant. After implantation, the cap is remodeled into the body's own tissue and provides a cushion for the neuroma. As host cells infiltrate the biomaterial, it is converted into a form of connective tissue. Axons and Schwann cells will also infiltrate from the stump. As fibroblasts (and other cells supporting remodeling into a connective tissue) 1) migrate and proliferate faster than Schwann cells/axons and 2) infiltrate from multiple sides and 3) axonal regeneration stops when it encounters other tissues (such as muscle, connective tissue layers, etc); the device will result in a layer of connective tissue surrounding a small neuroma in a vascularized tissue capsule. This capsule provides the desired isolation and protection.

All patents, patent applications, provisional applications, and publications referred to or cited herein are incorporated by reference in their entirety, including all figures and tables, to the extent they are not inconsistent with the explicit teachings of this specification.

We claim:

1. A sterile device for protecting against a neuroma forming at a stump of a transected nerve, wherein the device comprises:
    a body having an open proximal end and, integrally formed with the body, a closed distal end wherein the body of the device is less than 100 mm in diameter and less than 500 mm in length;
    wherein the body, including the closed distal end, defines an internal chamber, without openings other than at the proximal end, thereby inhibiting axonal escape from the device when the device is implanted on the nerve stump by inserting the nerve stump through the opening in the proximal end; and
    one or more separators within the internal chamber that divide the internal chamber thereby creating a plurality of separate volumes into which regenerating axons grow such that one or more regenerating axons are physically separated from one or more other regenerating axons;
    and wherein the device comprises a biomaterial that remodels into a tissue cushion after implantation.

2. The device according to claim 1, wherein the device comprises a biomaterial selected from the group consisting of: high density polyethylene (HDPE), polyethylene glycol (PEG) hydrogel, and purified proteins from human or sources.

3. The device according to claim 1, wherein the device comprises a biomaterial selected from the group consisting of small intestine submucosa (SIS), amnion, dermis, collagen and decellularized fascia.

4. The device according to claim 1, wherein the body is cylindrical in shape.

5. A method for protecting against neuromas comprising: inserting and securing a nerve stump into a device of claim 1.

* * * * *